United States Patent [19]

Crabbe et al.

[11] 3,969,412
[45] July 13, 1976

[54] 16,17-SECO-DELTA 4,9(10) AND -DELTA 4,9(10),11 STEROIDS

[75] Inventors: Pierre Crabbe, Mexico City, Mexico; John A. Edwards, Los Altos; John H. Fried, Palo Alto, both of Calif.

[73] Assignee: Syntex (U.S.A.) Inc., Palo Alto, Calif.

[22] Filed: Nov. 22, 1974

[21] Appl. No.: 526,359

Related U.S. Application Data

[60] Continuation of Ser. No. 440,328, Feb. 7, 1974, abandoned, which is a division of Ser. No. 142,762, May 12, 1971, Pat. No. 3,819,686.

[52] U.S. Cl. .......................... 260/586 E; 260/345.9; 260/347.8; 260/590 R
[51] Int. Cl.$^2$ .......................................... C07C 49/48
[58] Field of Search .......... 260/586 E, 345.9, 347.8, 260/590

[56] References Cited
UNITED STATES PATENTS

| 2,830,074 | 4/1958 | Farinacchi | 260/586 E |
| 3,192,257 | 6/1965 | Zderic | 260/586 E |

OTHER PUBLICATIONS

Chem. Abstr. 61:14750(h)–17751(b) (1964).
Chem. Abstr. 63:13347(d)–13348(g) (1965).
Chem. Abstr. 67:91020–91021 (1967).
Chem. Abstr. 70:68610(z) (1969).

*Primary Examiner*—Gerald A. Schwartz
*Attorney, Agent, or Firm*—Tom M. Moran; Joseph I. Hirsch

[57] ABSTRACT

The novel 16,17-secoestra-4,9(10)-diene, 16,17-secoestra-4,9(10),11-triene, 16,17-secogona-4,9(10)-diene and 16,17-secogona-4,9(10)-triene compounds and the 14β-isomers thereof useful as antiandrogenic agents, and methods for their preparation.

8 Claims, No Drawings

16,17-SECO-DELTA 4,9(10) AND -DELTA 4,9(10),11 STEROIDS

This is a continuation, of application Ser. No. 440,328 filed Feb. 7, 1974, abandoned, which was a division of application Ser. No. 142,762 filed May 12, 1971, now U.S. Pat. No. 3,819,686 issued June 25, 1974.

The present invention relates to novel 16,17-seco steroids of the estrane and gonane series.

More particularly, this invention relates to certain novel 16,17-secoestra-4,9(10)-dienes, 16,17-secoestr-4,9(10),11-trienes and the 13-alkyl-gonadiene and gonatriene derivatives thereof.

These compounds are represented by the formula:

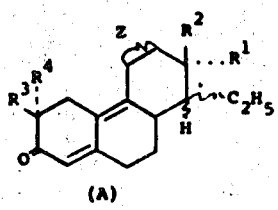

(A)

wherein $R^1$ represents carboxy and the conventionally hydrolyzable esters thereof, acetyl, lower alkyl, hydroxymethyl and the conventional hydrolyzable esters and ethers thereof, or a hydroxylated hydrocarbon radical represented by the formulas:

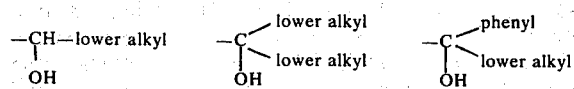

and the conventionally hydrolyzable esters and ethers thereof, $R^2$ represents lower alkyl;

$R^3$ and $R^4$ represent hydrogen or methyl, provided that $R^4$ is methyl when $R^3$ is methyl, and Z is a carbon-carbon single bond or a carbon-carbon double bond.

These compounds have asymmetric carbon atoms and the various steroisomers are included within the scope of this invention.

The term "lower alkyl" as used herein refers to straight or branched alkyl groups containing up to 4 carbon atoms, e.g. methyl, ethyl, n-propyl, isopropyl, n-butyl, and the like.

The term "conventional hydrolyzable esters and ethers" as used herein refers to hydrolyzable carboxylic ester and ether groups known conventionally in the art. These hydrolyzable carboxylic esters are derived from both substituted and unsubstituted hydrocarbon carboxylic acids. These acids can be completely saturated or possess varying degrees of unsaturation (including aromatic), can be of straight chain, branched chain, or cyclic structure, and preferably contain from 1 to 12 carbon atoms. In addition, they can be substituted by functional groups, for example, hydroxy, alkoxy containing up to six carbon atoms, acyloxy containing up to 12 carbon atoms, nitro, amino, halogeno, and the like, attached to the hydrocarbon backbone chain. Typical ester groups include acetate, propionate, butyrate, trimethylacetate, valerate, methylethylacetate, caproate, t-butylacetate, 3-methylpentanoate, enanthate, caprylate, trimethylacetate, pelargonate, decanoate, undecenoate, benzoate, phenylacetate, diphenylacetate, cyclopentylpropionate, methoxyacetate, aminoacetate, diethylaminoacetate, trichloroacetate, β-chloropropionate, bicyclo-[2.2.2]-octane-1'-carboxylate, adamantoate, and the like. Typical ether groups are methyl ether, ethyl ether, cyclopentyl ether, cyclohexyl ether, propyl ether, tetrahydropyran-2'-yl ether, tetrahydrofuran-2'-yl ether, 4'-methoxy-tetrahydropyran-4'-yl ether, propyl ether, and the like.

The compounds of the present invention are valuable pharmaceutical agents possessing anti-androgenic activity. They are of particular utility for the treatment of hyperandrogenic conditions, such as acne, prostatic hypertrophy, hirsutism in the female, seborreic dermatis and the like.

The compounds of the present invention are obtained by a process illustrated by the following reaction sequence:

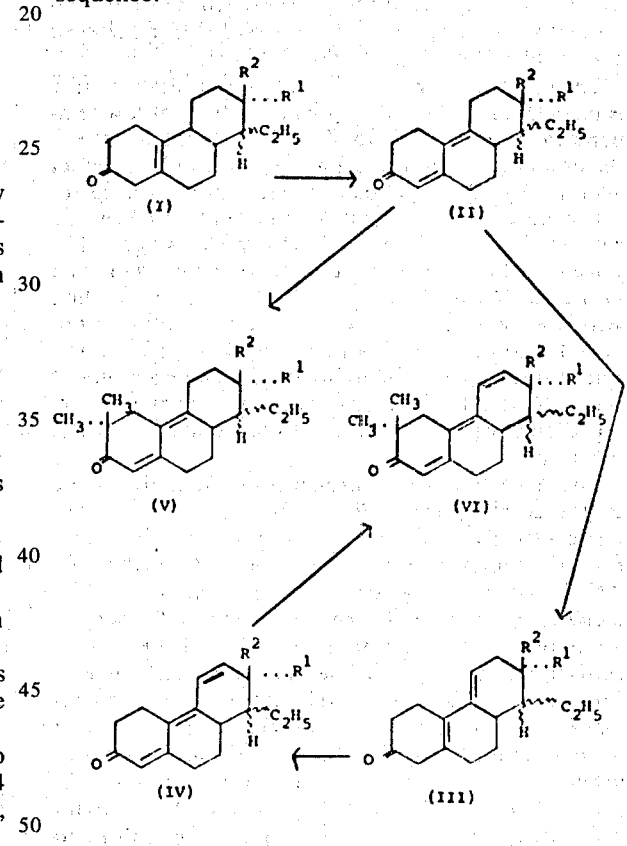

wherein $R^1$ and $R^2$ have the above-indicated meaning: the wavy lines at C-14 indicate the α or β configuration (each and mixtures) for the hydrogen atom and the ethyl group at said position.

In practicing the process illustrated above a 3-keto-16,17-secoestr-5(10)-ene, 3-keto-16,17-secogon-5(10)-ene or the 14β-isomers thereof is treated with bromine in pyridine or preferably with pyridinium perbromide hydrobromide in pyridine solution, to produce the corresponding $\Delta^{4,9(10)}$ compound of formula II. The amount of pyridinium perbromide hydrobromide may vary between approximately 1 to approximately 10 molar equivalents of the reagent, preferably about 1.1 molar equivalents, using a large excess of pyridine as solvent. The reaction is carried out at a temperature comprised between −10°C. and room temperature, for a period of time of the order of one to several hours. Lower temperatures are also operative, however the reaction is slower. Similarly, temperatures higher than room temperature are also operative, but tend to produce in some cases undesirable by-products.

Treatment of a $\Delta^{4,9(10)}$ compound (II) with acetyl chloride in a lower alcohol such as methanol or ethanol affords the corresponding $\Delta^{5(10),9(11)}$ isomer (III) which upon reaction with a quinone, using particularly 2,3-dichloro-5,6-dicyano-1,4-benzoquinone in dioxane solution, affords the estra-4,9(10),11-triene or 13-alkyl-gona-4,9(10), 11-triene compound (IV) or the 14β-isomers thereof.

In the case of using a free 17-hydroxylated compound as starting material, it is advisable to protect said group prior to the reaction with acetyl chloride, by conventional esterification or by formation of the tetrahydropyranyl-ether, hydrolyzing the protecting group once the $\Delta^{4,9(10),11}$-triene has been formed. Similarly, it is preferred to use an ester of a 17-carboxylic acid rather than the free acid.

The reaction of the $\Delta^{4,9(10)}$-diene with acetyl chloride is carried out under anhydrous conditions at low temperature between −20° to 0°C., for a period of time of the order of 30 minutes to 2 hours, preferably for about 45 minutes. This reaction can be followed by ultraviolet spectrum measurements of aliquots taken every 10 minutes. When the reaction is complete, which is followed by the change of the ultraviolet spectrum from 308 μ to 240 μ, the product is isolated by extraction with a solvent non-miscible with water. The amount of acetyl chloride used is not critical, however, it is preferred to use at least one molar equivalent per mol of diene: particularly good results are obtained using equal amounts of the steroidal compound and acetyl chloride.

The $\Delta^{5(10),9(11)}$-diene is unstable and isomerizes back to the $\Delta^{4,9(10)}$ starting diene; therefore, it is recommended to carry out the next step reaction with quinone right after the isolation of intermediate (III). The $\Delta^{5(10),9(11)}$-diene is treated with an excess of 2,3-dichloro-5,6-dicyano-1,4-benzoquinone in dioxane solution using preferably from about 2 to about 4 molar equivalents of the quinone per mol of starting material. This dehydrogenation is conducted at room temperature for a period of time of between approximately 3 to approximately 20 hours. The reaction can also be followed by ultraviolet spectrum measurements of aliquots taken every hour until the band of 240 μ disappears, changing the absorption to 232 and 338 μ, to afford the compounds of formula IV.

The product is isolated from the reaction mixture by conventional techniques, e.g. by separation of the hydroquinone formed during the reaction by decantation or filtration, evaporation of the filtrate to dryness and purification of the residue by chromatography on alumina.

When a 17-acyloxylated compound is used and a free 17-hydroxy compound is desired, the acyloxy group is hydrolyzed by conventional treatment with base. When the 17-hydroxy group has been protected as a tetrahydropyranyl ether the protecting group can be hydrolyzed by acid treatment, for example by treatment with hydrochloric acid in methanol solution.

The 17-hydroxylated compounds of formulas II and IV can be esterified or etherified following the conventional esterification and etherification methods known to the skilled in the art, i.e., esterification with an acid anhydride or acid chloride in pyridine solution for the esterification of primary and secondary hydroxyl groups and with carboxylic acid anhydrides in benzene solution and in the presence of an acid catalyst such as p-toluenesulfonic acid or with a mixture of a carboxylic acid-carboxylic anhydride in the presence of an acid catalyst for the compounds having tertiary hydroxyl groups.

Etherification is also carried out by conventional techniques. Thus, reaction with dihydropyran, dihydrofuran or 4-methoxy-5,6-dihydro-2H-pyran in an inert solvent such as benzene and in the presence of an acid catalyst produces the tetrahydropyran-2'-yloxy, tetrahydrofuran-2'-yloxy or 4'-methoxytetrahydropyran-4'-yloxy derivatives, respectively. Methyl, ethyl and cyclopentyl ethers, for example, are prepared upon reaction of the hydroxy compound with sodium hydride and methyl iodide, ethyl iodide and cyclopentyl bromide, respectively.

Compounds of formulas II and IV wherein R= hydroxymethyl can be converted in the corresponding acids (II and IV, R= COOH) by oxidation with chromium trioxide, and the acids can be esterified by conventional methods, such as treatment with an excess of a diazoalkane such as diazomethane or diazoethane in ether solution.

Compounds of formulas II and IV are converted into the 2α-monomethyl and 2,2-dimethyl derivatives by reaction with a methyl halide such as methyl iodide in the presence of potassium t-butoxide, using a mixture of toluene-hexamethylphosphoramide as solvent. The reaction is carried out at a temperature below 0°C., and preferably between −10° to −70°C., adding a solution of potassium t-butoxide in t-butanol to a previously cooled mixture of the steroid and methyl iodide in toluene-hexamethylphosphoramide.

The reaction mixture is maintained at said temperature for a period of time of between 30 minutes and several hours, preferably between 4 and 6 hours, isolating the product by conventional techniques such as by dilution with water, separation of the organic phase and evaporation of the solvents under reduced pressure, or by steam distillation of the solvents followed by extraction of the product with an organic solvent non-miscible with water such as ethyl acetate or methylene chloride.

The $\Delta^{5(10)}$ starting materials for the process object of the present invention are obtained from 3-methoxy-16,17-secoestra-1,3,5(10)-trien-17-oic acid methyl ester, 3-methoxy-16,17-seco-14β-estra-1,3,5(10)-trien-17-oic acid methyl ester and the corresponding 18-alkyl derivatives thereof (16,17-seco-13-alkyl gonatrienes) in accordance with our copending application SER. No. 142,763 filed on May 12, 1971 and entitled 16,17-Seco-$\Delta^4$ and -$\Delta^{5(10)}$ Steroids, (PA-491) now Pat. No. 3,839,420.

Briefly, the methods for producing the same are as follows:

16,17-secoestr-5(10)-en-17-ol-3-one is obtained from 3-methoxy-16,17-secoestra-1,3,5(10)-trien-17-ol.

The latter, upon reduction of the aromatic ring under Birch conditions, i.e. using an alkali metal such as lith-

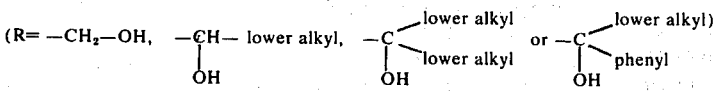

ium in liquid ammonia, followed by hydrolysis of the 3-methoxy-2,5(10)-diene intermediate with oxalic acid in aqueous methanol furnishes the desired 16,17-seco-estr-5(10)-en-17-ol-3-one. Alternatively, the Birch reduction can be performed on the 17-oic acid followed by reduction to the 17-ol or on the 17-oic acid methyl ester to furnish the 17-ol compound.

Oxidation of 16,17-secoestr-5(10)-en-17-ol-3-one with 8N chromium trioxide in sulfuric acid or chromium trioxide in pyridine gives rise to 3-keto-16,17-secoestr-5(10)-en-17-oic acid, which in turn is esterified by reaction with an excess of a diazoalkane.

By refluxing 3-methoxy-16,17-secoestra-1,3,5(10)-trien-17-oic methyl ester with an excess of a lower alkyl magnesium halide such as methylmagnesium bromide, ethylmagnesium bromide, isopropylmagnesium bromide and the like in an inert organic solvent for a period of time of the order of 15 to 24 hours, the corresponding 3-methoxy-17-keto-17-alkyl-16,17-secoestra-1,3,5(10)-triene compound is produced in mixture with the 3-methoxy-17-hydroxy-17,17-dialkyl compound.

When a 3-methoxy-17-keto-17-alkyl-16,17-secoestra-1,3,5(10)-triene is treated with phenyl lithium in tetrahydrofuran solution or with phenylmagnesium bromide in ether solution, at reflux temperature, there is obtained the 3-methoxy-17-hydroxy-17-alkyl-17-phenyl-16,17-secoestra-1,3,5(10)-triene compound.

Reduction of a 3-methoxy-17-keto-17-alkyl-16,17-secoestra-1,3,5(10)-triene with an alkali metal in liquid ammonia followed by mild hydrolysis of the $\Delta^{2,5(10)}$-diene produced, i.e., using oxalic acid in aqueous methanol affords the corresponding 17-hydroxy-17-alkyl-16,17-secoestr-5(10)-en-3-one compound.

Similarly, by reduction of the 17-trisubstituted compounds, i.e., 3-methoxy-17-hydroxy-17,17-dialkyl-16,17-secoestra-1,3,5(10)-triene compounds and 3-methoxy-17-hydroxy-17-alkyl-17-phenyl-16,17-secoestra-1,3,5(10)-triene compound with an alkali metal in liquid ammonia followed by hydrolysis with oxalic acid the corresponding 17-hydroxy-17,17-dialkyl-16,17-secoestr-5(10)-en-3-one and 17-hydroxy-17-alkyl-17-phenyl-16,17-secoestr-5(10)-en-3-one compounds are produced.

17-Acetyl-16,17-secoestr-5(10)-en-3-one is obtained by oxidation of 17-hydroxy-17-methyl-16,17-secoestr-5(10)-en-3-one with chromium trioxide in pyridine.

Oxidation of 3-methoxy-16,17-secoestra-1,3,5(10)-trien-17-ol with chromium trioxide in pyridine or with a 8N solution of chromic acid in acetone and in the presence of sulfuric acid (Jones reagent) gives rise to the corresponding 3-methoxy-16,17-secoestra-1,3,5(10)-trien-17-al which is then reduced by chemical or electrochemical methods to the corresponding 17-unsubstituted compound i.e. 3-methoxy-16,17-secoestra-1,3,5(10)-triene.

The 17-unsubstituted compound is then converted into 16,17-secoestr-5(10)-en-3-one by reduction under Birch conditions followed by hydrolysis with oxalic acid.

Similarly, electrochemical or chemical carbonyl reduction of a 3-methoxy-17-keto-17-alkyl-16,17-secoestra-1,3,5(10)-triene compound e.g. 3-methoxy-17-keto-17-methyl-16,17-secoestra-1,3,5(10)-triene produces the corresponding compounds substituted at C-17 by an alkyl group e.g. 3-methoxy-17-methyl-16,17-secoestra-1,3,5(10)-triene, which in turn is reduced with an alkaline metal in liquid ammonia and the 2,5(10)-diene intermediate hydrolyzed with oxalic acid to afford the corresponding 17-alkyl-16,17-secoestr-5(10)-en-3-one e.g. 17-methyl-16,17-secoestr-5(10)-en-3-one. Chemical carbonyl reduction can be accomplished by, for example, a Wolff-Kishner reduction, a Clemmensen reduction, or thioketal formation followed by treatment with Raney nickel.

The 14β-isomers of the above mentioned compounds as well as the 18-alkylated derivatives (13-alkyl-gon-5(10)-enes) are obtained in a similar manner, starting from 3-methoxy-16,17-seco-14β-estra-1,3,5(10)-trien-17-oic acid methyl ester, a 3-methoxy-13-alkyl-16,17-secogona-1,3,5(10)-trien-17-oic methyl ester or the 14β-isomers of the last mentioned compounds.

3-Methoxy-16,17-seco-14β-estra-1,3,5(10)-trien-17-oic acid methyl ester and the 18-alkyl derivatives thereof are in turn obtained from 14β-estrone or an 18-alkyl derivative thereof, by conversion into the enol acetate, treatment of the latter compound with osmium tetroxide followed by decomposition of the osmate ester with sodium bisulfite to give the 16α-hydroxy-3-methoxy-14β-estra-1,3,5(10)-trien-17-ne (16α-hydroxy-14β-estrone) or an 18-alkyl derivative, which upon reaction with 1.1 molar equivalents of periodic acid in aqueous pyridine affords a 3-methoxy-16-hydroxy-17-oxa-17α-keto-D-homo-14β-estra-triene or the 18-substituted derivative. Treatment of the lactol thus obtained with an excess of an ethereal solution of diazomethane or with metyl iodide in methanol gives rise to 3-methoxy-16,17-seco-14β-estra-1,3,5(10)-trien-16-aldehyde-17-oic acid methyl ester which is reduced by chemical or electrochemical methods to 3-methoxy-16,17-seco-14β-estra-1,3,5(10)-trien-17-oil acid methyl ester or the corresponding gonatriene compound. Particularly, the eliminaion of the aldehyde group is carried out by converting said group into the benzyl thio acetal upon reaction with benzyl mercaptan in ether and in the presence of boron trifluoride etherate, followed by desulfurization with Raney nickel.

The following Examples illustrate but are not intended to limit the scope of the present invention.

PREPARATION 1

Part A — A mixture of 300 g. of potassium hydroxide and 45 ml. of water is heated to 260°C. in a nickel crucible, 10 g. of estradiol are added and the temperature is then raised to 290°–300°C., maintaining this temperature during 45 minutes. At the end of this time, the foaming mass formed is allowed to cool to room temperature, water is added and the reaction mixture let stand at said temperature overnight so the excess of potassium hydroxide dissolved. The aqueous solution is filtered through Celite, (diatomaceous earth), and the filtrate is made acidic by the addition of an excess of concentrated hydrochloric acid. The precipitate which forms is collected by filtration, washed with water and air dried, to produce 16,17-secoestra-1,3,5(10)-trien-3-ol-17-oic acid (trans doisynolic acid).

Part B — A solution of 42 g. of 16,17-secoestra-1,3,5(10)-trien-3-ol-17-oic acid in 400 ml. of ethanol is heated to 30°–40°C. and treated in an alternative manner with 240 ml. of dimethylsulfate in 240 ml. of methanol and 40% aqueous potassium hydroxide solution, in such a way that the pH of the reaction mixture is maintained alkaline.

After the addition, the reaction mixture is stirred at the same temperature for 2 hours further, water is added and the product extracted with methylene chloride, the organic extract is washed with water to neutral, dried and evaporated to dryness. The solid residue is purified by filtration through 210 g. of Florisil, using hexane as eluant, thus yielding 3-methoxy-16,17-secoestra-1,3,5(10)-trien-17-oic acid methyl ester.

Part C — A solution of 18 g. of 3-methoxy-17-carbomethoxy-16,17-secoestra-1,3,5(10)-triene in 200 ml. of anhydrous tetrahydrofuran is added dropwise, under stirring to 18 g. of lithium aluminum hydride in 300 ml. of anhydrous tetrahydrofuran and the reaction mixture is refluxed for 3 hours. The reaction mixture is then cooled and the excess reagent destroyed by careful addition of saturated solution of sodium sulfate and solid sodium sulfate. The resulting mixture is filtered through Celite diatomaceous earth and the filtrate extracted several times with methylene chloride; the combined organic extracts are washed to neutral, dried over sodium sulfate and evaporated to dryness. Chromatography of the residue on silica gel, using hexane:ethyl acetate (60:40) as eluant affords 3-methoxy-16,17-secoestra-1,3,5(10)-trien-17-ol.

Part D — A solution of 16.5 g. of 3-methoxy-16,17-secoestra-1,3,5(10)-trien-17-ol in 500 ml. of anhydrous tetrahydrofuran is added in a steady stream to 1.5 liters of liquid ammonia. To the resulting stirred solution are added 16.5 g. of lithium in portions, and the resulting blue solution is stirred for 1 hour further. Methanol is then added dropwise until the blue color is discharged and the ammonia is allowed to evaporate. The product is then extracted with ethyl acetate and the combined organic extracts washed with water to neutral, dried over sodium sulfate and evaporated to dryness under reduced pressure, to give 3-methoxy-16,17-secoestra-2,5(10)-dien-17-ol.

Part E — A solution of 15 g. of 3-methoxy-16,17-secoestra-2,5(10)-dien-17-ol in 1280 ml. of methanol is treated with 19.5 g. of oxalic acid dissolved in 250 ml. of water. The reaction mixture is kept at room temperature for 45 minutes, diluted with ice water and extracted with methylene chloride. The organic extracts are washed with sodium bicarbonate solution and water to neutrality, dried over sodium sulfate and evaporated to dryness under vacuo. Crystallization of the residue from acetone-hexane affords 16,17-secoestr-5(10)-en-17-ol-3-one.

By the same methods starting from 18-methylestradiol and 18-ethyl estradiol, there are obtained as final products 13-ethyl-16,17-secogon-5(10)-en-17-ol-3-one and 13-n-propyl-16,17-secogon-5(10)-en-17-ol-3-one, respectively.

PREPARATION 2

A solution of 16 g. of 3-methoxy-16,17-secoestra-1,3,5(10)-trien-17-oic acid methyl ester in 250 ml. of anhydrous tetrahydrofuran is treated with an excess (approximately 200 ml.) of 4N methylmagnesium bromide in ether and the mixture is refluxed with the exclusion of moisture for 18 hours. The cooled mixture is cautiously treated with excess aqueous ammonium chloride solution and the product isolated by extraction with methylene chloride. The extract is washed with water, dried over sodium sulfate and evaporated to dryness. The residue is purified by t.l.c. using a mixture of hexane-ethyl acetate (95:5) to produce 3-methoxy-17-methyl-16,17-secoestra-1,3,5(10)-trien-17-one and 3-methoxy-17,17-dimetyl-16,17-secoestra-1,3,5(10)-trien-17-ol.

By the same method but using 3-methoxy-13-ethyl-16,17-secogona-1,3,5(10)-trien-17-oic acid methyl ester and 3-methoxy-13-n-propyl-16,17-secongona-1,3,5(10)-trien-17-oic acid methyl ester as starting materials, there are obtained respectively 3-methoxy-13-ethyl-17-metyl-16,17-secogona-1,3,5(10)-trien-17-one and 3-methoxy-13-ethyl-17,17-dimethyl-16,17-secogona-1,3,5(10)-trien-17-ol; and 3-methoxy-13-n-propyl-17-methyl-16,17-secogona-1,3,5(10)-trien-17-one and 3-methoxy-13-n-propyl-17,17-dimethyl-16,17-secogona-1,3,5(10)-trien-17-ol.

The 17-methyl and 17,17-dimethyl compounds thus obtained are treated in accordance with the methods of Parts D and E of Preparation 1, to produce respectively:

17-methyl-16,17-secoestr-5(10)-en-17-ol-3-one,
17,17-dimethyl-16,17-secoestr-5(10)-en-17-ol-3-one,
13-ethyl-17-methyl-16,17-secogon-5(10)-en-17-ol-3-one,
13-ethyl-17,17-dimetyl-16,17-secogon-5(10)-en-17-ol-3-one,
13-n-propyl-17-metyl-16,17-secogon-5(10)-en-17-ol-3-one, and
13-n-propyl-17,17-dimethyl-16,17-secogon-5(10)-en-17-ol-3-one.

PREPARATION 3

Part A — A solution of 10 g. of 3-methoxy-16,17-secoestra-1,3,5(10)-trien-17-ol in 200 ml. of acetone distilled over potassium permanganate is cooled to 10°C. and treated under an atmosphere of nitrogen and with stirring, with a solution of 8N chromic acid (prepared by mixing 26 g. of chromium trioxide with 23 ml. of concentrated sulfuric acid and diluting with water to 100 ml.), until the color of the reagent persisted in the mixture. It is stirred for 10 minutes further at the same temperature and diluted with sodium bisulfite solution and water. The product is then extracted with methylene chloride and the organic extract washed with water, dried over sodium sulfate and evaporated under vacuum, thus affording a crude product which upon recrystallization from acetone-hexane gives 3-methoxy-16,17-secoestra-1,3,5(10)-trien-17-al.

A solution of 6 g. of 3-methoxy-16,17-secoestra-1,3,5(10)-trien-17-ol in 120 ml. of pyridine is added to a mixture of 6 g. of chromic trioxide in 20 ml. of pyridine. The reaction mixture is allowed to stand at room temperature for 15 hours, diluted with ethyl acetate and filtered through Celite diatomaceous earth. The filtrate is washed well with water, dried and evaporated to dryness to yield 3-methoxy-16,17-secoestra-1,3,5(10)-trien-17-al which may be further purified by recrystallization from acetone:hexane.

Part B — Into the cathode compartment of a divided electrolysis cell provided with a cellulose dialysis membrane, lead electrodes (each electrode measuring 2 cm × 5 cm × 1.6 mm) and a stirrer, is added 4.15 g. of 3-methoxy-16,17-secoestra-1,3,5(10)-trien-17-al and a mixture of 600 ml. of dioxane and 500 ml. of 10% aqueous sulfuric acid (by weight). To the anode compartment is added 40 ml. of the mixture of dioxane and 10% aqueous sulfuric acid. A current density of 0.8 amps./cm$^2$ is applied for a period of six hours. The reaction mixture is then removed from the cell and concentrated under reduced ressure to a small volume which is then extracted several times with ether. The ether extracts are combined, washed with water and a 5% aqueous sodium bicabonate solution, dried and evaporated to dryness to furnish 3-methoxy-16,17-secoestra-1,3,5(10)-triene.

The foregoing reactions are repeated with the exception of using 3-methoxy-13-ethyl-16,17-secogona-1,3,5(10)-trien-17-ol and 3-methoxy-13-n-propyl-16,17-secogona-1,3,5(10)-trien-17-ol as starting materials, to yield 3-methoxy-13-ethyl-16,17-secogona-1,3,5(10)-triene and 3-methoxy-13-n-propyl-16,17-secogona-1,3,5(10)-triene, respectively.

In accordance with the electrochemical reduction set forth in Part B of this Preparation, 3-methoxy-17-methyl-16,17-secoestra-1,3,5(10)-trien-trien-17-one and 3-methoxy-13-ethyl-17-methyl-16,17-secogona-1,3,5(10)-trien-17-one are convereted into the corresponding desoxy compounds namely 3-methoxy-17-methyl-16,17-secoestra-1,3,5(10)-triene and 3-methoxy-13-ethyl-17-methyl-16,17-secogona-1,3,5(10)-triene.

The 17-desoxy compounds thus obtained are in turn reduced with lithium in liquid ammonia, in accordance with Part D of Preparation 1, and the 3-methoxy-$\Delta^{2,5(10)}$-intermediates hydrolyzed with oxalic acid, as established in Part E of said Preparation to yield respectively 16,17-secoestr-5(10)-en-3-one, 13-ethyl-16,17-secogon-5(10)-en-3-one, 13-n-propyl-16,17-secogon-5(10)-en-3-one, 17-methyl-16,17-secoestr-5-(10)-en-3-one and 13-ethyl-17-methyl-16,17-secogon-5(10)-en-3-one.

PREPARATION 4

A solution of 2 g. of 3-methoxy-17-methyl-16,17-secoestra-1,3,5(10)-trien-17-one in 250 ml. of anhydrous tetrahydrofuran is added dropwise to a solution of 10 molar equivalents of phenyl lithium in 150 ml. of ether with mechanical stirring and under an atmosphere of nitrogen. The mixture is then refluxed for 5 hours, cooled, poured into ice water and acidified with hydrochloric acid, stirring vigorously for 1 hour. The product is then extracted with methylene chloride and the organic extracts washed with water to neutral, dried over sodium sulfate and evaporated to dryness. Recrystallization of the residue from acetone-hexane yields 3-methoxy-17-methyl-17-phenyl-16,17-secoestra-1,3,5(10)-trien-17-ol.

Upon reduction of 3-methoxy-17-methyl-17-phenyl-16,17-secoestra-1,3,5(10)-trien-17-ol with lithium in liquid ammonia followed by hydrolysis of the $\Delta^{2,5(10)}$-diene intermediate with oxalic acid, in accordance with the methods of Preparation 1, parts D and E, 17-methyl-17-phenyl-16,17-secoestr-5(10)-en-17-ol-3-one is obtained.

In a similar manner, 3-methoxy-13-ethyl-17-methyl-16,17-secogona-1,3,5(10)-trien-17-one and 3-methoxy-13-n-propyl-17-methyl-16,17-secogona-1,3,5(10)-trien-17-one are converted respectively into 13-ethyl-17-methyl-17-phenyl-16,17-secogon-5(10)-en-17-ol-3-one and 13-n-propyl-17-methyl-17-phenyl-16,17-secogon-5(10)-en-17-ol-3-one.

PREPARATION 5

A solution of 1 g. of 17-methyl-17-hydroxy-16,17-secoestr-5(10)-en-3-one in 20 ml. of pyridine is added to a mixture of 1 g. of chromium trioxide in 20 ml. of pyridine. The reaction mixture is allowed to stand at room temperature for 18 hours, and then diluted with ethyl acetate and filtered through Celite, diatomaceous earth, washing the solid with hot ethyl acetate. The combined filtrates are washed well with water, dried over sodium sulfate and evaporated to dryness, thus producing 17-methyl-16,17-secoestr-5(10)-en-3,17-dione which is purified by crystallization from acetone-ether.

Likewise, 13-ethyl-17-methyl-17-hydroxy-16,17-secogon-5(10)-en-17-ol-3-one and 13-n-propyl-17-methyl-17-hdyroxy-16,17-secogon-5(10)-en-17-ol-3-one are converted respectively into 13-ethyl-17-methyl-16,17-secogon-5(10)-en-3,17-dione and 13-n-propyl-17-methyl-16,17-secogon-5(10)-en-3,17-dione.

PREPARATION 6

Preparation 2 is repeated with the exception of using ethereal ethylmagnesium bromide and n-propylmagnesium bromide as reagents instead of methylmagnesium bromide, to produce as final products 17-ethyl-17-hydroxy-16,17-secoestr-5(10)-en-3-one and 17,17-diethyl-17-hydroxy-16,17-secoestr-5(10)-en-3-one, and 17-propyl-17-hydroxy-16,17-secoestr-5(10)-en-3-one and 17,17-dipropyl-17-hydroxy-16,17-secoestr-5(10)-en-3-one, respectively.

PREPARATION 7

A mixture of 5 g. of 14β-estrone and 3-methylether, 75 ml. of isopropenyl acetate and 0.8 g. of p-toluenesulfonic acid is heated to reflux temperature and the reaction mixture is refluxed for 18 hours using a water separator, at the end of which time the resulting solution is cooled, diluted with ethyl acetate and washed with water, sodium bicarbonate solution and water to neutrality, dried over sodium sulfate and evaporated to dryness under vacuo, to yield 3-methoxy-17-acetoxy-14β-estra-1,3,5(10),16-tetraene which may be purified by crystallization from acetone-ether.

To a solution of 3 g. of 3-methoxy-17-acetoxy-14β-estra-1,3,5(10),16-tetraene in 60 ml. of pyridine are added 4 g. of osmium tetroxide and the reaction mixture is kept at room temperature for 48 hours, under stirring. Then, 8 g. of sodium bisulfite dissolved in 120 ml. of water and 80 ml. of pyridine are added, and the mixture is stirred at room temperature for 24 hours further. The product is then extracted with ethyl acetate, and the combined organic extracts washed with water to neutral, dried and evaporated to dryness. The residue is purified by t.l.c. eluting the product with hexane-ethyl acetate 75:25 thus producing 3-methoxy-14β-estra-1,3,5(10)-trien-16α-ol-17-one.

A solution of 1.19 g. of 3-methoxy-14β-estra-1,3,5(10)-trien-16α-ol-17-one in 20 ml. of pyridine is treated, at room temperature with 915 mg. (one molar equivalent) of periodic acid (HIO$_4$.2H$_2$O) dissolved in 10 ml. of water. The reaction mixture is kept at room temperature for 20 hours, and the solvent is then eliminated under reduced pressure, taking care that the temperature is maintained below 30°C. The residue is extracted with ethyl acetate and the organic extracts are washed with 5% sodium bicarbonate solution, 5% sodium thiosulfate solution and water, dried over sodium sulfate and evaporated to dryness under vacuo, to yield 3-methoxy-16-hydroxy-17-oxa-17α-keto-D-homo-14β-estra-1,3,5(10)-triene, which is used for the next step without further purification.

A solution of the foregoing crude lactol in 20 ml. of methylene chloride is treated with 20 ml. of an ethereal solution of diazomethane, and the mixture is kept at room temperature for one hour. The excess diazomethane is then destroyed by adding a few drops of acectic acid, the solvents are eliminated under vacuo and the residue is purified by t.l.c., to yield 3-methoxy-16,17-seco-14β-estra-1,3,5(10)-trien-16-al-17-oic acid methyl ester.

To a solution of 1 g. of 3-methoxy-16,17-seco-14β-estra-1,3,5(10)-trien-16-al-17-oic acid methyl ester in 5 ml. of ethyl ether are added 0.5 ml. of benzyl mercaptan and three drops of boron trifluoride etherate, and the mixture is kept at room temperature for 20 hours. It is then diluted with ether and the ethereal solution washed several times with 5% potassium hydroxide solution and water to neutral, dried and evaporated to dryness. The residue is dissolved in 150 ml. of ethanol, 5 g. of Raney nickel are added and the mixture is then refluxed through Celite diatomaceous earth and the nickel is washed well with hot ethanol. The combined filtrate and washings are evaporated to dryness, and the residue purified by chromatography on Florisil, thus producing 3-methoxy-16,17-seco-14β-estra-1,3,5(10)-trien-17-oic acid methyl ester.

In a similar manner, starting from 3-methoxy-13-ethyl-14β-gona-1,3,5(10)-trien-17-one, there is obtained 3-methoxy-13-ethyl-16,17-seco-14β-gona-1,3,5(10)-trien-17-oic acid methyl ester as final product.

In accordance with the procedure set forth in Preparation 1, Parts C, D, and E, 3-methoxy-16,17-seco-14β-estra-1,3,5(10)-trien-17-oic acid methyl ester and 3-methoxy-13-ethyl-16,17-16,17-seco-14β-gona-1,3,5(10)-trien-17-oic acid methyl ester are converted respectively into 16,17-seco-14β-estr-5(10)-en-17-ol-3-one and 13-ethyl-16,17-seco-14β-gon-5(10)-en-17-ol-3-one.

PREPARATION 8

Preparations 2 to 6 are repeated using the 14β-isomers of the starting materials used therein, thus producing the corresponding 14β-products thereof, e.g.

17-methyl-17-hydroxy-16,17-seco-14β-estr-5(10)-en-3-one, 17,17-dimethyl-17-hydroxy-16,17-seco-14β-estr-5(10)-en-3-one, 13-ethyl-17-methyl-17-hydroxy-16,17-seco-14β-gon-5(10)-en-3-one, 13-ethyl-17,17-dimethyl-17-hydroxy-16,17-seco-14β-gon-5(10)-en-3-one, 16,17-seco-14β-estr-5(10)-en-3-one, 13-ethyl-16,17-seco-14β-gon-5(10)-en-3-one, 17-methyl-16,17-seco-14β-gon-5(10)-en-3-one, 17-methyl-17-phenyl-16,17-seco-14β-estr-5(10)-en-17-ol-3-one, 17-methyl-16,17-seco-14β-estr-5(10)-en-3,17-dione, 17-ethyl-17-hydroxy-16,17-seco-14β-estr-5(10)-en-3-one and 17,17-diethyl-17-hydroxy-16,17-seco-14β-estr-5(10)-en-3-one.

EXAMPLE 1

A solution of 4.3 g. of 16,17-secoestr-5(10)-en-17-ol-3-one in 110 ml. of pyridine is cooled to 0°C. and treated with 5.07 g. of pyridinium perbromide hydrobromide. The reaction mixture is stirred at 0°C. for 1 hour, and at room temperature for an hour further. It is then diluted with ice water and extracted with methylene chloride. The organic extracts are washed succesively with dilute hydrochloric acid, water, 5% sodium bicarbonate solution and water until neutral, dried over sodium sulfate and evaporated to dryness under reduced pressure. The crude product is purified by t.l.c. with hexane:ethyl acetate 60:40 to yield 16,17-secoestra-4,9(10)-dien-17-ol-3-one which may be crystallized from ether-pentane.

EXAMPLE 2

A mixture of 8.6 g. of 16,17-secoestra-4,9(10)-dien-17-ol-3-one, 60 ml. of pyridine and 30 ml. of acetic anhydride is kept at room temperature for 18 hours. The mixture is then poured into ice water, and the formed precipitate collected by filtration, washed with water, and dried. Crystallization from ether affords 17-acetoxy-16,17-secoestra-4,9(10)-dien-3-one in pure form.

A solution of 10 g. of 17-acetoxy-16,17-secoestra-4,9(10)-dien-3-one in 600 ml. of anhydrous ethanol is cooled to −10°C. and treated dropwise, under stirring with 15 ml. of acetyl chloride. The reaction mixture is stirred at the same temperature for 35 minures diluted with water and extracted with methylene chloride. The organic extracts are washed to neutrality, dried and evaporated to dryness, thus affording 17-acetoxy-16,17-secoestra-5(10),9(11)-dien-3-one, which is used for the next step without further purification.

To a solution of 6.25 g. of the foregoing product in 142 ml. of dioxane are added 11.5 g. of 2,3-dichloro-5,6-dicyano-1,4-benzoquinone and the resulting mixture is stirred at room temperature for 18 hours. It is then diluted with methylene chloride and the solid material separated by filtration. The filtrate is evaporated to dryness and the residue chromatographed on neutral alumina, to produce 17-acetoxy-16,17-secoestr-4,9(10),11-trien-3-one.

EXAMPLE 3

A solution of 1.1 g. of 17-acetoxy-16,17-secoestra-4,9(10),11-trien-3-one in 50 ml. of methanol is treated with 500 mg. of potassium hydroxide dissolved in 1 ml. of water and the reaction mixture is kept at room temperature for 30 minutes. It is then poured into ice water and the product extracted with ethyl acetate. The organic extract is washed with water to neutral, dried and evaporated to dryness, to give a crude compound which upon recrystallization from methylene chloride ether affords 16,17-secoestra-4,9(10),11-trien-17-ol-3-one.

EXAMPLE 4

To a cold solution of 4.5 g. of 16,17-secoestra-4,9(10of pyridine is added 17-ol-3-one in 120 ml. of 15 ml. of heptanoyl chloride and the reaction mixture is allowed to stand for 18 hours at room temperature. The reaction mixture is then concentrated to a small volume under vacuo, diluted with water and extracted with methylene chloride; the organic extracts are washed with water to neutrality, dried over sodium sulfate and evaporated to dryness under reduced pressure. Crystallization of the residue from acetone-hexane gives 17-heptanoyloxy-16,17-secoestra-4,9(10)-dien-3-one.

To a stirred solution of 2 g. of 17-heptanoyloxy-16,17-secoestra-4,9(10)-dien-3-one in 120 ml. of anhydrous ethanol cooled to −10°C., are added dropwise, in a 5 minutes period, 2 ml. of acetyl chloride, and the reaction mixture is stirred for 30 minutes further at the same temperature, taking aliquots every 10 minutes to determine the ultraviolet absorption, which changes from 308 mμ to 240 mμ. The reaction mixture is then diluted with water and the product isolated by extraction with methylene chloride. The organic extract is washed with water to neutral, dried and evaporated to dryness under vacuo, to yield 17-heptanoyloxy-16,17-secoestra-5(10),9(11)-dien-3-one.

A mixture of 780 mg. of 17-heptanoyloxy-16,17-secoestra-5(10),9(11)-dien-3-one, 17 ml. of dioxane and 1.43 g. of 2,3-dichloro-5,6-dicyano-1,4-benzoquinone is stirred at room temperature for 15 hours. It is then diluted with methylene chloride and the solid separated by filtration. The filtrate is evaporated to dryness and purified by t.l.c. using hexane:ethyl acetate 70:30, thus obtaining 17-heptanoyloxy-16,17-secoestra-4,9(10),11-trien-3-one.

EXAMPLE 5

In accordance with the method of Example 1, the following compounds are prepared:
13-ethyl-16,17-secogona-4,9(10)-dien-17-ol-3-one,
13-n-propyl-16,17-secogona-4,9(10)-dien-17-ol-3-one,
17-methyl-16,17-secoestra-4,9(10)-dien-17-ol-3-one,
17,17-dimethyl-16,17-secoestra-4,9(10)-dien-17-ol-3-one,
13-ethyl-17-methyl-16,17-secogona-4,9(10)-dien-17-ol-3-one,
13-ethyl-17,17-dimethyl-16,17-secogona-4,9(10)-dien-17-ol-3-one,
13-n-propyl-17-methyl-16,17-secogona-4,9(10)-dien-17-ol-3-one,
16,17-secogona-4,9(10)-dien-3-one,
13-ethyl-16,17-secogona-4,9(10)-dien-3-one,
13-n-propyl-16,17-secogona-4,9(10)-dien-3-one,
17-methyl-16,17-secoestra-4,9(10)-dien-3-one,
13-ethyl-17-methyl-16,17-secogona-4,9(10)-dien-3-one,
17-methyl-17-phenyl-16,17-secoestra-4,9(10)-dien-17-ol-3-one,
13-ethyl-17-methyl-17-phenyl-16,17-secogona-4,9(10)-dien-17-ol-3-one,
17-methyl-16,17-secoestra-4,9(10)-dien-3,17-dione,
13-ethyl-17-methyl-16,17-secogona-4,9(10)-diene-3,17-dione,
13-n-propyl-17-methyl-16,17-secogona-4,9(10)-diene-3,17-dione,
17-ethyl-16,17-secoestra-4,9(10)-dien-17-ol-3-one,
17-propyl-16,17-secoestra-4,9(10)-dien-17-ol-3-one,
17,17-dipropyl-16,17-secoestra-4,9(10)-dien-17-ol-3-one,
16,17-seco-14β-estra-4,9(10)-dien-17-ol-3-one,
13-ethyl-16,17-seco-14β-gona-4,9(10)-dien-17-ol-3-one,
17-methyl-16,17-seco-14β-estra-4,9(10)-dien-17-ol-3-one,
17,17-dimethyl-16,17-seco-14β-estra-4,9(10)-dien-17-ol-3-one and 16,17-seco-14β-estra-4,9(10)-dien-3-one, starting from the corresponding Δ$^{5(10)}$ compounds.

EXAMPLE 6

In accordance with the esterification procedure of Example 2, 13-ethyl-16,17-secogona-4,9(10)-dien-17-ol-3-one, 13-n-propyl-16,17-secogona-4,9(10)-dien-17-ol-3-one, 17-methyl-16,17-secoestra-4,9(10)-dien-17-ol-3-one, 13-ethyl-17-methyl-16,17-secogona-4,9(10)-dien-17-ol-3-one, 13-n-propyl-17-methyl-16,17-secogona-4,9(10)-dien-17-ol-3-one, 16,17-seco-14β-estra-4,9(10)-dien-17-ol-3-one, 17-ethyl-16,17-seco-14β-estra-4,9(10)-dien-17-ol-3-one and 17-methyl-16,17-seco-14β-estra-4,9(10)-dien-17-ol-3-one are converted into the corresponding acetates.

EXAMPLE 7

A mixture of 1 g. of 17,17-dimethyl-16,17-secoestra-4,9(10)-dien-17-ol-3-one, 2 ml. of acetic anhydride, 5 ml. of acetic acid and 1 g. of p-toluenesulfonic acid is kept at room temperature for 2 hours. The reaction mixture is then diluted with water, extracted with methylene chloride and the organic extracts washed with water, sodium carbonate solution and water to neutrality, dried over sodium sulfate and evaporated to dryness under vacuo. Crystallization of the residue from acetone-ether gives 17,17-dimethyl-17-acetoxy-16,17-secoestra-4,9(10)-dien-3-one.

By using propionic anhydride and enanthic anhydride in place of acetic anhydride the corresponding propionate and enanthate of 17,17-dimethyl-17-hydroxy-16,17-secoestra4,9(10)-dien-3-one are obtained.

In a similar manner are produced the acetates, propionates, and enanthates of 13-ethyl-17,17-dimethyl-16,17-secogona-4,9(10)-dien-17-ol-3-one, 17-methyl-17-phenyl-16,17-secoestra-4,9(10)-dien-17-ol-3-one and 13-ethyl-17-methyl-17-phenyl-16,17-secogona-4,9(10)-dien-17-ol-3-one.

EXAMPLE 8

Two milliliters of dihydropyran are added to a solution of 1 g. of 16,17-secoestra-4,9(10)-dien-17-ol-3-one in 15 ml. of benzene. About 1 ml. is distilled to remove moisture and 0.4 g. of p-toluenesulfonyl chloride is added to the cooled solution. This mixture is allowed to stand at room temperature for 4 days, and is then washed with aqueous sodium carbonate solution and water, dried and evaporated. The residue is chromatographed on neutral alumina, eluting with hexane and hexane-ether 80:20 to yield 17-tetrahydropyran-2'-yloxy-16,17-secoestra-4,9(10)-dien-3-one.

Upon reaction of 17-tetrahydropyran-2'-yloxy-16,17-secoestra-4,9(10)-dien-3-one with acetyl chloride in accordance with the method of Example 2, 17-tetrahydropyran-2'-yloxy-16,17-secoestra-5(10),9(11)-dien-3-one is produced, which is converted into 17-tetrahydropyran-2'-yloxy-16,17-secoestra-4,9(10),11-trien-3-one by treatment with 2,3-dichloro-5,6-dicyano-1,4-benzoquinone.

To a solution of 500 mg. of 17-tetrahydropyran-2'-yloxy-16,17-secoestra-4,9(10),11-trien-3-one in 10 ml. of methanol is added 0.1 ml. of concentrated hydrochloric acid and the reaction mixture is kept at room temperature for 3 hours. It is then diluted with water and the formed precipitate collected by filtration, washed with water and air dried, thus obtaining 16,17-secoestra-4,9(10),11-trien-17-ol, identical to the product obtained in Example 3.

EXAMPLE 9

In accordance with the method of Example 2, the 17-acetoxy compounds obtained in Example 6 are converted into the corresponding $\Delta^{5(10),9(11)}$-isomers, which upon reaction with 2,3-dichloro-5,6-dicyano-1,4-benzoquinone, by following the dehydrogenation method set forth in said Example, produce:

17-acetoxy-13-ethyl-16,17-secogona-4,9(10),11-trien-3-one, 17-acetoxy-13-n-propyl-16,17-secogona-4,9(10),11-trien-3-one, 17-acetoxy-17-methyl-16,17-secoestra-4,9(10),11-trien-3-one, 17-acetoxy-13-ethyl-17-methyl-16,17-secogona-4,9(10),11-trien-3-one, 17-acetoxy-13-n-propyl-17-methyl-16,17-secogona-4,9(10),11-trien-3-one, 17-acetoxy-16,17-seco-14β-estra-4,9(10),11-trien-3-one, 17-acetoxy-13-ethyl-16,17-seco-14β-gona-4,9(10),11-trien-3-one, and 17-acetoxy-17-methyl-16,17-seco-14β-estra-4,9(10),11-trien-3-one, respectively.

The foregoing trienes are hydrolyzed to the corresponding free 17-hydroxy compounds by following the method of Example 3.

EXAMPLE 10

A solution of 1 g. of 16,17-secoestra-4,9(10)-dien-3-one in 75 ml. of anhydrous ethanol is cooled to −20°C. and 1.5 ml. of acetyl chloride are added. The reaction mixture is stirred at the same temperature for 1 hour, diluted with water and extracted with methylene chloride. The organic extracts are washed with water to neutral, dried and evaporated to dryness, to yield 16,17-secoestra-5(10),9(11)-dien-3-one.

To a solution of 750 mg. of 16,17-secoestra-5(10),9(11)-dien-3-one in 20 ml. of dioxane are added 1.4 g. of 2,3-dichloro-5,6-dicyano-1,4-benzoquinone, and the reaction mixture is stirred at room temperature for 10 hours. It is then diluted with methylene chloride, the hydroquinone formed filtered off and the filtrate evaporated to dryness. The residue is purified by t.l.c. to give 16,17-secoestra-4,9(10),11-trien-3-one.

In a similar fashion, from the corresponding $\Delta^{4,9(10)}$-dienes are obtained:

13-ethyl-16,17-secogona-4,9(10),11-trien-3-one,
13-n-propyl-16,17-secogona-4,9(10),11-trien-3-one,
17-methyl-16,17-secoestra-4,9(10),11-trien-3-one,
13-ethyl-17-methyl-16,17-secogona-4,9(10),11-trien-3-one,
17-methyl-16,17-secoestra-4,9(10),11-triene-3,17-dione,
13-ethyl-17-methyl-16,17-secogona-4,9(10),11-triene-3,17-dione,
13-n-propyl-16,17-secogona-4,9(10),11-triene-3,17-dione, and
16,17-seco-14β-estra-4,9(10)-dien-3-one.

EXAMPLE 11

By following the method of Example 2, 17,17-dimethyl-17-acetoxy-16,17-secoestra-4,9(10)-dien-3-one is converted into 17,17-dimethyl-17-acetoxy-16,17-secoestra-4,9(10),11-trien-3-one.

A mixture of 1 g. of 17,17-dimethyl-17-acetoxy-16,17-secoestra-4,9(10),11-trien-3-one, 100 ml. of methanol and 0.5 g. of potassium hydroxide dissolved in 1 ml. of water is refluxed for 1 hour. It is then neutralized with acetic acid and concentrated to a small volume under reduced pressure. Water is then added and the product separated by filtration, washed with water and dried thus obtaining 17,17-dimethyl-16,17-secoestra-4,9(10),11-trien-17-ol-3-one.

EXAMPLE 12

In accordance with the method of Example 8, 16,17-seco-14β-estra-4,9(10),11-trien-17-ol-3-one, 13-ethyl-16,17-secogona-4,9-(10),11-trien-17-ol-3one, 17-methyl-16,17-secoestra-4,9(10),11-trien-17-ol-3-one and 17-methyl-17-phenyl-16,17-secoestra-4,9(10)-dien-17-ol-3one are converted into the corresponding tetrahydropyranylethers.

EXAMPLE 13

Two milliliters of dihydrofuran are added to a solution of 1 g. of 16,17-secoestra-4,9(10),11-trien-17-ol-3-one in 15 ml. of benzene. About 1 ml. is distilled to remove moisture and 0.4 g. of p-toluenesulfonyl chloride is added to the cooled solution. This mixture is allowed to stand at room temperature for four days, and is then washed with aqueous sodium carbonate solution and water, dried and evaporated. The residue is chromatographed on neutral alumina, eluting with hexane, to yield 17-tetrahydrofuran-2'-yloxy-16,17-secoestra-4,9(10),11-trien-3-one which is recrystallized from pentane.

Similarly, 17-(4'-methoxy-tetrahydropyran-4'-yloxy)-16,17-secoestra-4,9(10),11-trien-3-one is prepared by utilization of the foregoing procedure employing 4-methoxy-5,6-dihydro-2H-pyran in lieu of dihydrofuran.

By the same method, the 17-tetrahydrofuranyl and 17-(4'-methoxy-tetrahydropyranyl) ethers of the starting hydroxy compounds of Example 12 are prepared.

EXAMPLE 14

A solution of one chemical equivalent of 16,17-secoestra-4,9(10),11-trien-17-ol-3-one in 30 ml. of benzene is heated to reflux and about 2 ml. removed by distillation to eliminate moisture. The mixture is cooled to room temperature and two chemical equivalents of sodium hydride are added, followed by the dropwise addition of two chemical equivalents of cyclopentyl bromide in 10 ml. of benzene, over a period of 20 minutes. The mixture is allowed to reflux for 20 hours after which time the precipitate of sodium bromide is removed by filtration and the organic phase dried and evaporated to yield 17-cyclopentyloxy-16,17-secoestra-4,9(10),11-trien-3-one which is further purified upon recrystallization from pentane.

Alternatively, methyl iodide and ethyl iodide can be used in lieu of cyclopentyl bromide to produce 17-methoxy-16,17-secoestra-4,9(10),11-trien-3-one and 17-ethoxy-16,17-secoestra-4,9(10),11-trien-3-one respectively.

Likewise, the 17-cyclopentyl, methyl and ethyl ethers of 16,17-secoestra-4,9-(10)-dien-17-ol-3-one and 13-ethyl-16,17-secogona-4,9(10),11-trien-17-ol-3-one are obtained.

EXAMPLE 15

A solution of 5 g. of 17-tetrahydropyran-2'-yloxy-16,17-secoestra-4,9(10),11-trien-3-one in 100 ml. of anhydrous toluene and 50 ml. of anhydrous hexamethylphosphoramide is cooled to −25°C. in a dry ice-acetone bath, 6.5 ml. of methyl iodide are added and to the cooled mixture is added dropwise in a 20 minute period, a previously prepared solution of 2 g. of potassium metal in 50 ml. of t-butanol under stirring and under an atmosphere of nitrogen. The reaction mixture is stirred for 4 hours further at the same temperature, under nitrogen. It is then diluted with water and the solvents eliminated by steam distillation. The produce is extracted with methylene chloride and the organic extract washed with water to neutral, dried over sodium sulfate and evaporated to dryness under vacuo. The residue is dissolved in methanol (100 ml.) containing 1 ml. of 5% hydrochloric acid and boiled for 10 minutes. The reaction mixture is neutralized with dilute sodium hydroxide and evaporated to a small volume. Water is added and the product is isolated by extraction with methylene chloride. The residue is purified by chromatography on Florisil, to yield 2,2-dimethyl-17-acetoxy-16,17-secoestra-4,9(10),11-trien-3-one, and 2α-methyl-17-acetoxy-16,17-secoestra-4,9(10),11-trien-3-one.

A mixture of 1 g. of 2,2-dimethyl-17-hydroxy-16,17-secoestra-4,9(10),11-trien-3-one, 4 ml. of pyridine and 2 ml. of acetic anhydride is allowed to stand at room temperature for 15 hours. The mixture is then poured into ice water and the solid which forms is collected by filtration, washed with water and dried to yield 2,2-dimethyl-17-acetoxy-16,17-secoestra-4,9(10),11-trien-3-one which may be further purified through recrystallization from acetone:hexane.

Similarly, 2α-methyl-17-acetoxy-16,17-secoestra-4,9-(10),11-trien-3-one is prepared.

By the same method, the following compounds are prepared from the respective starting compounds:

2,2-dimethyl-16,17-secoestra-4,9(10),11-trien-3-one, 2,2-dimethyl-17-methoxy-16,17-secoestra-4,9(10),11-trien-3-one, 2,2,17-trimethyl-16,17-secoestra-4,9(10),11-trien-3-one, 2,2-dimethyl-13-ethyl-16,17-secogona-4,9(10),11-trien-3-one, 2,2-dimethyl-17-tetrahydropyran-2'-yloxy-16,17-secoestra-4,9(10),11-trien-3-one, 2,2,17,17-tetramethyl-17-acetoxy-16,17-secoestra-4,9(10),11-trien-3-one, 2,2-dimethyl-17-acetoxy-16,17-seco-14β-estra-4,9(10),11-trien-3-one, 2,2-dimethyl-13-ethyl-16,17-seco-14β-gona-4,9(10),11-trien-3-one, 2,2-dimethyl-16,17-seco-14β-estra-4,9(10),11-trien-3-one, 2,2-dimethyl-17-heptanoyloxy-16,17-secoestra-4,9(10)-dien-3-one, 2,2,17-trimethyl-13-ethyl-16,17-secogone-4,9(10)-dien-3-one, 2,2,17-trimethyl-17-acetoxy-16,17-secoestra-4,9(10)-dien-3-one, 2,2,17-trimethyl-13-ethyl-16,17-secogona-4,9(10)-diene-3,17-dione, 2,2,17-trimethyl-13-n-propyl-16,17-secogona-4,9(10)-dien-3,17-dione, 2,2-dimethyl-17-ethyl-17-acetoxy-16,17-secoestra-4,9(10)-dien-3-one, 2,2-dimethyl-17-propyl-17-acetoxy-16,17-secoestra-4,9(10)-dien-3-one, 2,2-dimethyl-17,17-dipropyl-17-acetoxy-16,17-secoestra-4,9(10)-dien-3-one, 2,2-dimethyl-17-acetoxy-16,17-seco-14β-estra-4,9(10)-dien-3-one, 2,2-dimethyl-13-ethyl-17-acetoxy-16,17-seco-14β-gona-4,9(10)-dien-3-one, 2,2,17-trimethyl-17-acetoxy-16,17-seco-14β-estra-4,9(10)-dien-3-one, 2,2,17-tetramethyl-17-acetoxy-16,17-seco-14β-estra-4,9(10)-dien-3-one, and 2,2-dimethyl-16,17-seco-14β-estra-4,9(10)-dien-3-one.

EXAMPLE 16

A solution of 2 g. of 2,2-dimethyl-17-acetoxy-16,17-secoestra-4,9(10),11-trien-3-one in 100 ml. of methanol is treated with a solution of 500 mg. of potassium hydroxide in 5 ml. of water and the reaction mixture kept at room temperature for 1 hour. It is then diluted with water and extracted with ethyl acetate, the organic extract is washed with water to neutral, dried over sodium sulfate and evaporated to dryness under vacuo, thus producing 2,2-dimethyl-16,17-secoestra-4,9(10),11-trien-17-ol-3-one.

In a similar manner are hydrolyzed other 2,2-dimethyl-17-acetoxy compounds obtained in Example 15, e.g. 2,2-dimethyl-17-acetoxy-16,17-seco-14β-estra-4,9(10),11-trien-3-one, 2,2-dimethyl-17-ethyl-17-acetoxy-16,17-secoestra-4,9(10)-dien-3-one, 2,2,17-trimethyl-17-acetoxy-16,17-secoestra-4,9(10)-dien-3-one and 2,2-dimethyl-17-acetoxy-16,17-seco-14β-estra-4,9(10)-dien-3-one to produce the corresponding 17-hydroxy compounds, i.e. 2,2-dimethyl-16,17-seco-14β-estra-4,9(10),11-trien-17-ol-3-one, 2,2-dimethyl-17-ethyl-16,17-secoestra-4,9(10)-dien-17-ol-3-one, 2,2,17-trimethyl-16,17-secoestra-4,9(10)-dien-17-ol-3-one, and 2,2-dimethyl-16,17-seco-14β-estra-4,9(10)-dien-17-ol-3-one.

EXAMPLE 17

The 17-hydroxy compounds obtained in Example 16 are etherified with dihydropyran and dihydrofuran, in accordance with the methods of Examples 8 and 13, to yield the corresponding tetrahydropyran-2'-yloxy and tetrahydrofuran-2'-yloxy derivatives. EXAMPLE 18

A solution of 2 g. of 16,17-secoestra-4,9(10),11-trien-17-ol-3-one in 40 ml. of pyridine is added to a mixture of 1 g. of chromium trioxide in 40 ml. of pyridine. The reaction mixture is allowed to stand at room temperature for 18 hours, and the diluted with ethyl acetate and filtered through Celite, diatomaceous earth, washing the solid with hot ethyl acetate. The combined filtrates are washed well with 5% hydrochloric acid solution and water, dried over sodium sulfate and evaporated to dryness. The residue is purified by t.l.c., to yield the pure 3-keto-16,17-secoestra-4,9(10),11-trien-17-oic acid.

To a solution of 1 g. of 3-keto-16,17-secoestra-4,9(10),11-trien-17-oic acid in 20 ml. of ether is added 20 ml. of an ethereal solution of diazomethane, and the mixture is kept at room temperature for 1 hour. The excess diazomethane is then destroyed by adding a few drops of acetic acid, and the solvent eliminated under vacuo, thus obtaining 3-keto-16,17-secoestra-4,9(10),11-trien-17-oic acid methyl ester.

By the same methods, 16,17-secoestra-4,9(10)-dien-17-ol-3-one, 13-ethyl-16,17-secogona-4,9(10),11-trien-17-ol-3-one, 16,17-seco-14β-estra-4,9(10)-dien-17-ol-3-one and 2,2-dimethyl-16,17-secoestra-4,9(10),11-trien-17-ol-3-one are converted first into the corresponding acids, and then into the methyl esters.

When using diazoethane in lieu of diazomethane, the ethyl esters are obtained.

EXAMPLE 19

To a solution of 1 g. of 17-acetoxy-16,17-secoestra-4,9(10),11-trien-3-one in 28 ml. of anhydrous tetrahydrofuran cooled to −35°C. is added dropwise under an atmosphere of nitrogen, 8 ml. of methyl iodide, and the mixture is stirred for 1.5 hours at −35° to −30°C. The mixture is then treated at the same temperature with a previously prepared mixture of 4 g. of potassium t-butoxide, 28.5 ml. of anhydrous tetrahydrofuran and 11 ml. of hexamethylphosphoramide. The reaction mixture is stirred at room temperature for an additional hour, diluted with water and extracted with methylene chloride. The combined organic extracts are washed with water to neutral, dried over sodium sulfate and evaporated to dryness. The residue is purified by t.l.c., using hexane-ethyl acetate, 80:20 as gradient to yield 2α,2β-dimethyl-17-acetoxy-16,17-secoestra-4,9(10),11-triene-3-one and 2α-methyl-17-acetoxy-16,17-secoestra-4,9(10),11-trien-3 -one.

17-Acetoxy-16,17-secoestra-4,9(10),11-trien-3-one (200 mg.) in 560 ml. of anhydrous tetrahydrofuran is placed under a nitrogen atmosphere with 113 ml. of methyl iodide. The mixture is maintained at −35°C. (± 5°) while a solution of 57 g. of potassium t-butoxide, 570 ml. of tetrahydrofuran, and 140 ml. of hexamethylphosphortriamide is added thereto with stirring over 1.5 hours. The mixture is then allowed to stand at room temperature for 1 hour after which time it is poured into water and extracted with petroleum ether. The extracts are washed with water and evaporated to dryness in vacuum to give 2α,2β-dimethyl-17-acetoxy-16,17-secoestra-4,9(10),11-trien-3-one, and 2α-methyl-17-acetoxy-16,17-secoestra-4,9(10),11-trien-3-one.

What is claimed is:

1. A compound selected from the group of compounds represented by the following formula:

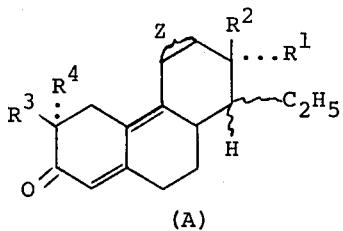

(A)

wherein $R^1$ represents a conventional hydrolyzable ether of a hydroxylated hydrocarbon radical represented by the formulas:

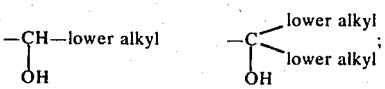

$R^2$ is lower alkyl;

$R^3$ and $R^4$ are hydrogen or methyl, provided that $R^4$ is methyl when $R^3$ is methyl; and Z is a carbon-carbon single bond or a carbon-carbon double bond.

2. A compound according to claim 1 wherein the hydrogen atom at C-14 is in α configuration.

3. A compound according to claim 1 wherein the hydrogen atom at C-14 is in β-configuration.

4. A compound according to claim 1 wherein Z is a carbon-carbon single bond.

5. A compound according to claim 1 wherein Z is a carbon-carbon double bond.

6. A compound according to claim 2 wherein $R^1$ is an ether of hydroxymethyl.

7. The compound according to claim 1 wherein said ethers are selected from the group consisting of the methyl ether, ethyl ether, cyclopentyl ether, tetrahydrofuran-2′-yl ether, and 4′-methoxy-tetrahydropyran-4′-yl ether.

8. The compound according to claim 1 wherein said compound is selected from the group consisting of 17-tetrahydropyran-2′yloxy-16,17-secoestra-4,9(10),11-trien-3-one, 17-tetrahydrofuran-2′-yloxy-16,17-secoestra-4,9(10),11-trien-3-one and 17-(4′-methoxy-tetrahydropyran-4′-yloxy)-16,17-secoestra-4,9(10),11-trien-3-one and 17-tetrahydropyran-2′-yloxy-16,17-secoestra-4,9(10)-dien-3-one.

* * * * *